(12) United States Patent
Lozano

(10) Patent No.: US 7,811,554 B2
(45) Date of Patent: Oct. 12, 2010

(54) HORSE LINIMENT

(76) Inventor: Flavio Lozano, 527 River La., Ruidoso Downs, NM (US) 88346

( * ) Notice: Subject to any disclaimer, the term of this patent is extended or adjusted under 35 U.S.C. 154(b) by 446 days.

(21) Appl. No.: 12/010,079

(22) Filed: Jan. 18, 2008

(65) Prior Publication Data

US 2008/0175933 A1    Jul. 24, 2008

Related U.S. Application Data

(60) Provisional application No. 60/881,180, filed on Jan. 19, 2007.

(51) Int. Cl.
*A61K 31/74* (2006.01)
*A61K 36/47* (2006.01)
*A61K 8/20* (2006.01)
*A61K 31/125* (2006.01)
*A01N 65/12* (2009.01)

(52) U.S. Cl. ............ 424/78.05; 424/764; 424/51; 424/698; 514/731; 514/692; 106/610

(58) Field of Classification Search ............ None
See application file for complete search history.

(56) References Cited

U.S. PATENT DOCUMENTS

| 224,031 | A |  | 2/1880 | Myers |
| 414,769 | A | * | 11/1889 | Gochenouer |
| 4,564,521 | A |  | 1/1986 | Altadonna |
| 4,582,706 | A | * | 4/1986 | Bailey |
| 4,822,595 | A | * | 4/1989 | Corliss et al. |
| 4,883,664 | A |  | 11/1989 | Sharkey |
| 5,124,320 | A |  | 6/1992 | Ivy et al. |
| 5,223,257 | A |  | 6/1993 | Arora |
| 5,853,768 | A |  | 12/1998 | Altadonna |
| 6,030,622 | A |  | 2/2000 | Shehadoh |
| 6,579,543 | B1 |  | 6/2003 | McClung |
| 6,733,794 | B1 |  | 5/2004 | Ingram et al. |
| 6,756,064 | B1 |  | 6/2004 | Carrol |
| 2006/0030621 | A1 |  | 2/2006 | Inaoka et al. |
| 2006/0051432 | A1 |  | 3/2006 | Morgan |

FOREIGN PATENT DOCUMENTS

| AU | 629945 B2 | * | 10/1992 |
| DE | 20111788 U1 | * | 3/2002 |

OTHER PUBLICATIONS

Delgado, G et al. Journal of Natural Products (Jun. 2001): 64(7): 861-864. Antiinflammatory constituents from Heterotheca inuloides.*
Hutchens, A Hankbook of Native American Herbs, 1992. Shambhala Publications, Inc., USA, pp. 7-9 and 76-78.*
Fetrow, CW et al. The Complete Guide to Herbal Medicines, 2000. Pocket Books, Inc., USA, pp. 32-33 and 131-133.*

* cited by examiner

*Primary Examiner*—Michele C. Flood
(74) *Attorney, Agent, or Firm*—Richard C. Litman

(57) ABSTRACT

The horse liniment is a veterinary composition for topical application for the relief of muscle and joint pain in horses. The composition contains, by weight, about 49% alcohol, 20% olive oil, 10% *arnica*, 14% creosote, 1% iodine, 2% turpentine, 2% camphor, and 2% alum. The ingredients may be mixed at room temperature, the powdered ingredients being soluble in the alcohol-olive oil base. The composition is applied topically to the affected muscles or joints in conventional manner as needed. The composition has been found to be effective, often with a single application, with increased range of motion, an absence or reduction of limping, increased energy, and other signs of a healthy, active horse.

15 Claims, No Drawings

HORSE LINIMENT

CROSS-REFERENCE TO RELATED APPLICATION

This application claims the benefit of U.S. Provisional Patent Application Ser. No. 60/881,180, filed Jan. 19, 2007.

BACKGROUND OF THE INVENTION

1. Field of the Invention

The present invention relates to veterinary medicaments, and particularly to a horse liniment for the relief of muscular and joint pain in horses.

2. Description of the Related Art

A good horse is a highly prized animal. Although the horse has been displaced by the automobile and farm machinery in developed countries, the horse is still used as a work animal on ranches and the like. Further, the horse is used for sports and recreation in thoroughbred racing, harness racing, show jumping, rodeos, recreational horseback riding, and other leisure time activities. Just like human beings, the horse's muscles can become sore and strained when subjected to intense exertion, or from being worked over extended periods of time. The problem may become exacerbated as the horse ages with the development of arthritis in the joints.

Various liniments have been developed over the years to provide soothing heat to sore and inflamed muscles and joints when giving the horse a rubdown after a hard workout or a long day of work. While the different formulations are effective to some degree, none have proven to be entirely satisfactory. Thus, a horse liniment solving the aforementioned problems is desired.

SUMMARY OF THE INVENTION

The horse liniment is a veterinary composition for topical application for the relief of muscle and joint pain in horses. The composition contains, by weight, about 49% alcohol, 20% olive oil, 10% arnica, 14% creosote, 1% iodine, 2% turpentine, 2% camphor, and 2% alum. The ingredients may be mixed at room temperature, the powdered ingredients being soluble in the alcohol-olive oil base. The composition is applied topically to the affected muscles or joints in conventional manner as needed. The composition has been found to be effective, often with a single application, with increased range of motion, an absence or reduction of limping, increased energy, and other signs of a healthy, active horse.

These and other features of the present invention will become readily apparent upon further review of the following specification.

DETAILED DESCRIPTION OF THE PREFERRED EMBODIMENTS

The present invention is a horse liniment that provides a veterinary composition for topical application for the relief of muscle and joint pain in horses. The composition contains, by weight, about 49% alcohol, 20% olive oil, 10% arnica, 14% creosote, 1% iodine, 2% turpentine, 2% camphor, and 2% alum. The ingredients may be mixed at room temperature, the powdered ingredients being soluble in the alcohol-olive oil base. The composition is applied topically to the affected muscles or joints in conventional manner as needed. The composition has been found to be effective, often with a single application, with increased range of motion, an absence or reduction of limping, increased energy, and other signs of a healthy, active horse.

The present composition is prepared with ethyl alcohol (ethanol), preferably prepared from sugar cane. More preferably, the liniment is prepared from grain alcohol (at least 190-proof), which has been found to be a more effective solvent than isopropyl or rubbing alcohol for mixing with the herbal components and extracting terpenoids and other beneficial compounds from the herbal components. Olive oil, which has a high content of oleic acid, has been used from ancient times for massages to keep muscles supple, to soothe aches and pains, and to heal minor abrasions.

Arnica is an herbal remedy noted in folk medicine for its anti-inflammatory effects when applied topically. Arnica may be derived from the flowers of the plant Arnica Montana. Alternatively, Arnica may be derived from the plant known as Mexican Arnica (also known as Heterotheca inuloides, False arnica or Arnica Mexicana), a plant common to Mexico and the Southwestern United States, including New Mexico. Both are reputed to exhibit the same anti-inflammatory effects when applied topically. Arnica is known to contain sesquiterpene lactones and esters thought to account for its anti-inflammatory activity, including arnicolide, helenalin, and dihydrohelenalin. In addition, Mexican Arnica contains the sesquiterpenoid lactones 7-hydroxy-3,4-dihydrocadalin and 7-hydroxycadalin. The mechanism of action is unknown, but is thought to relate to Arnica's antioxidant properties and counterirritant effect.

The creosote used in the horse liniment composition is not derived from pine oil or coal tar. Rather, creosote is derived from the creosote bush, Larrea tridenta, which is commonly known as chaparral. The creosote bush has long been used by Native Americans for medicinal purposes. The bush grows wild in arid regions of the Southwestern United States, and also in Mexico. Among other remedies, Native Americans would boil leaves and branches of the creosote bush to make a liniment for bruises and rheumatism. The leaf is available in powdered form, which dissolves in the alcohol-olive oil solvent at room temperature.

Tincture of iodine, oil of turpentine, camphor, and alum are well-known constituents of various liniments, and will not be discussed further.

It will be understood that the weight percentage composition described above is approximate, and descriptive of a preferred embodiment only. The scope of the horse liniment composition is intended to extend to compositions containing the components recited above, even though the weight percentages may vary from the percentages given.

The horse liniment is prepared by adding the iodine and turpentine to the alcohol, followed by the remaining ingredients. The composition is mixed to the desired strength at room temperature. The mixture is a free-flowing liquid.

The liniment may be applied to a horse showing signs of soreness due to an injury, to a horse showing fatigue after a workout, or to a horse showing signs of arthritis. The liniment may be applied as needed. The present inventor has found that after application of the liniment, the horse no longer shows signs of soreness, no longer limps, and no longer shows other signs of pain.

It is to be understood that the present invention is not limited to the embodiments described above, but encompasses any and all embodiments within the scope of the following claims.

I claim:

1. A horse liniment, comprising, by weight percent:
   about 49% alcohol;
   about 20% olive oil;

about 10% *Arnica*;
about 14% creosote;
about 1% iodine;
about 2% turpentine;
about 2% camphor; and
about 2% alum.

2. The horse liniment according to claim 1, wherein said alcohol comprises ethanol.

3. The horse liniment according to claim 1, wherein said alcohol comprises grain alcohol having a concentration of at least 190-proof.

4. The horse liniment according to claim 1, wherein said *arnica* is derived from flowers of *Arnica Montana*.

5. The horse liniment according to claim 1, wherein said *arnica* is derived from flowers of *Heterotheca inuloides*.

6. The horse liniment according to claim 1, wherein said creosote comprises powdered leaves from *Larrea tridenta*.

7. A horse liniment, consisting essentially of, by weight percent:
about 49% alcohol;
about 20% olive oil;
about 10% *Arnica*;
about 14% creosote;
about 1% iodine;
about 2% turpentine;
about 2% camphor; and
about 2% alum.

8. The horse liniment according to claim 7, wherein said alcohol comprises ethanol.

9. The horse liniment according to claim 7, wherein said alcohol comprises grain alcohol having a concentration of at least 190-proof.

10. The horse liniment according to claim 7, wherein said *arnica* is derived from flowers of *Arnica Montana*.

11. The horse liniment according to claim 7, wherein said *arnica* is derived from flowers of *Heterotheca inuloides*.

12. The horse liniment according to claim 7, wherein said creosote comprises powdered leaves from *Larrea tridenta*.

13. A horse liniment, comprising, by weight percent:
about 49% alcohol, the alcohol being at least 190-proof ethanol;
about 20% olive oil;
about 10% *Arnica*;
about 14% creosote derived from leaves of the creosote bush, *Larrea tridenta*;
about 1% iodine;
about 2% turpentine;
about 2% camphor; and
about 2% alum.

14. The horse liniment according to claim 13, wherein said *arnica* is derived from flowers of *Arnica Montana*.

15. The horse liniment according to claim 13, wherein said *arnica* is derived from flowers of *Heterotheca inuloides*.

* * * * *